(12) United States Patent
Jaffe

(10) Patent No.: US 8,017,160 B2
(45) Date of Patent: Sep. 13, 2011

(54) ENHANCEMENT OF MAGNESIUM UPTAKE IN MAMMALS

(76) Inventor: Russell Jaffe, Sterling, VA (US)

( * ) Notice: Subject to any disclaimer, the term of this patent is extended or adjusted under 35 U.S.C. 154(b) by 0 days.

(21) Appl. No.: 10/641,291

(22) Filed: Aug. 15, 2003

(65) Prior Publication Data

US 2005/0037998 A1 Feb. 17, 2005

(51) Int. Cl.
| | |
|---|---|
| A61K 33/06 | (2006.01) |
| A61K 31/19 | (2006.01) |
| A61K 31/28 | (2006.01) |
| A61K 31/685 | (2006.01) |
| A61K 33/14 | (2006.01) |
| A61K 47/00 | (2006.01) |

(52) U.S. Cl. ......... 424/682; 424/681; 424/686; 514/78; 514/492; 514/557; 514/772; 514/784; 514/785; 514/788

(58) Field of Classification Search .................. 424/682
See application file for complete search history.

(56) References Cited

U.S. PATENT DOCUMENTS

| | | | | |
|---|---|---|---|---|
| 2,694,664 | A | * 11/1954 | Maiese .................. | 514/669 |
| 4,064,234 | A | * 12/1977 | Howard .................. | 424/690 |
| 5,587,399 | A | 12/1996 | Acosta et al. ............ | 514/561 |
| 5,785,984 | A | * 7/1998 | Kurihara et al. .......... | 424/439 |

FOREIGN PATENT DOCUMENTS

| | | | |
|---|---|---|---|
| FR | 4608 M | * | 12/1966 |
| WO | WO 01/84961 A2 | | 11/2001 |

OTHER PUBLICATIONS

Gennaro et al., eds., Remington's Pharmaceutical Sciences (17th Ed. 1985), pp. 406,407,1014,1026,1308.*
Altura et al., Magnesium dietary intake modulates blood lipid levels and atherogenesis, Proc. Natl. Acad. Sci. USA (1990), vol. 87, pp. 1840-1844.*
PUBMED online, file Medline, PMID 69151 (Wurtman et al., Lecithin consumption raises serum-free-choline-levels, Lancet (1977), vol. 2, No. 8029, pp. 68-69), Abstract.*
Rinkel, "Supplementary European Search Report," 3 pages, from European patent application No. 04780786.2, European Patent Office, The Hague, Netherlands (dated Jun. 5, 2009).

* cited by examiner

*Primary Examiner* — Johann Richter
*Assistant Examiner* — Frank Choi
(74) *Attorney, Agent, or Firm* — Seyfarth Shaw LLP; John C. Serio

(57) ABSTRACT

Disclosed are methods and complexes for increasing magnesium uptake in mammals. Increasing magnesium uptake in mammals is accomplished by concurrently administering one or more magnesium salts with one or more quaternary amines and/or phosphatides and one or more di- or tri-carboxylic acids.

4 Claims, 1 Drawing Sheet

ENHANCEMENT OF MAGNESIUM UPTAKE IN MAMMALS

FIELD OF INVENTION

The present invention relates to increasing magnesium uptake in mammals. More particularly, the present inventions relates to increasing magnesium uptake in mammals by concurrently administering one or more magnesium salts, with one or more quaternary amines or phosphatides and one or more di- or tri-carboxylic acids.

BACKGROUND OF THE INVENTION

Magnesium is an important mineral in mammalian nutrition. As part of adenosine triphosphate (ATP), magnesium is used for all biosynthetic processes, glycolysis, formation of cyclic adenosine monophosphate (cyclic AMP), is involved in energy metabolism and energy dependent membrane transport and is used for ribonucleic acid (RNA) synthesis and transmission of the genetic code.

Magnesium, as a cation, is involved in over 10,000 enzyme (cell catalyst) actions. Magnesium is especially important to enzymes concerned with oxidative phosphorylation. Magnesium is also an important component of both intracellular and extracellular fluids. Intracellular magnesium is believed to control cellular metabolism by modulating the activity of rate limiting enzymes. Extracellular magnesium is important to the maintenance of electrical potentials of nerve and muscle membranes and for transmission of impulses across neuromuscular junctions. Magnesium has been shown to be important in maintaining the homeostasis of cardiac and smooth muscle tissues.

Magnesium is the fourth most common cation in the human body. For example, a typical human body contains on average 25 grams of magnesium. Approximately 59% of the magnesium is in the body's skeleton and bone structures, approximately 40% is in the body's musculature and soft body tissues and approximately 1% (about 2 to 2.8 grams) is in the body's extracellular fluid.

Considering that magnesium is an activator for so many important body functions, it is not surprising that deficiency can lead to a variety of serious physical and mental problems. Health conditions such as muscle spasms and tremors are associated with magnesium deficiency. In addition, nerve irritability, mood instability, high blood pressure (Essential, otherwise unexplained), angina (chest pain on exertion), heart arrythmias (magnesium is 'nature's calcium channel blocker') calcium loss/osteoporosis risk and insomnia are also associated with magnesium deficiency. Toxic metals (lead, mercury, cadmium, arsenic, and nickel) can accumulate more rapidly when magnesium stores are low and the replacement of magnesium in the body hastens elimination of toxic metals from the body.

Magnesium is inorganic and is not produced by the human body. Humans must rely upon dietary sources to provide the body with its magnesium requirements. Dietary magnesium intake has been declining in the United States, with a per capita decline of magnesium in the U.S. food supply (estimated as food flowing through the food distribution system) of from 408 mg./day in 1909 to 329 mg./day in 1986, almost a 20% decline. This decline has been attributed to the increase in consumption of processed foods. For example, 'white foods' such as refined flour, sugar, fat and processed or synthesized foods contain relatively little magnesium.

In those with normal digestion and assimilation, magnesium absorption from food is believed to be from approximately 40 to 60% of that ingested. However, there are many factors that can inhibit the body's ability to absorb magnesium. For example, phosphoric acid, which is present in most soft drinks, and oxalates in foods such as spinor and chocolate, combine with magnesium in the intestines and form insoluble compounds that are not absorbed by the body. Other factors that can reduce the function of the magnesium uptake system include: toxic minerals such as lead, mercury, arsenic, cadmium, and nickel; biocidal hormone mimics; metabolic cellular acidosis; phytates in ingested foods; caffeine intake; alcohol consumption; certain medications such as steroids and oral contraceptives; distress; enteropathy and other intestinal disorders; and maldigestion and digestive diseases.

Oral intakes of magnesium are difficult for the body to absorb. It is believed that only 3 to 12% of elemental magnesium, typically in the form of magnesium oxide, is absorbed for use by the body. Attempts have been made to make complexes to enhance the absorption of magnesium in the human body. For example, U.S. Pat. No. 5,849,337 to Dixon describes a complex containing magnesium, protein amino acids and ascorbic acid. As discussed above and in Dixon, a need exists for a method of increasing magnesium intake in mammals, particularly humans.

SUMMARY OF THE INVENTION

This invention includes magnesium complexes and methods of administering magnesium to a mammal.

The magnesium complex includes a magnesium salt, a quarternary amine or phosphatide and a di-carboxylic acid or tri-carboxylic acid. Preferably, the magnesium complex of claim 1, wherein the complex further includes a solution of water and glycerol.

Preferably, the magnesium salt is magnesium glycinate, magnesium ascorbate, magnesium chloride, magnesium sulfate, magnesium orotate, magnesium citrate, magnesium fumarate, magnesium malate, magnesium succinate, magnesium tartrate magnesium carbonate or similar magnesium salt. Preferably, the quarternary amine is choline and/or phosphatide is phosphatidyl choline and the di- or tri-carboxylic acid is citrate.

The method for enhancing magnesium uptake in mammals includes administering to a mammal a magnesium salt, a quaternary amine or phosphatide and a di-carboxylic acid or tri-carboxylic acid. Preferably, the administering is oral and the mammal is human.

BRIEF DESCRIPTION OF THE DRAWINGS

The invention will be better understood by reference to the Detailed Description of the Invention when taken together with the attached FIG. 1, wherein.

DETAILED DESCRIPTION OF THE INVENTION

Figure 1:
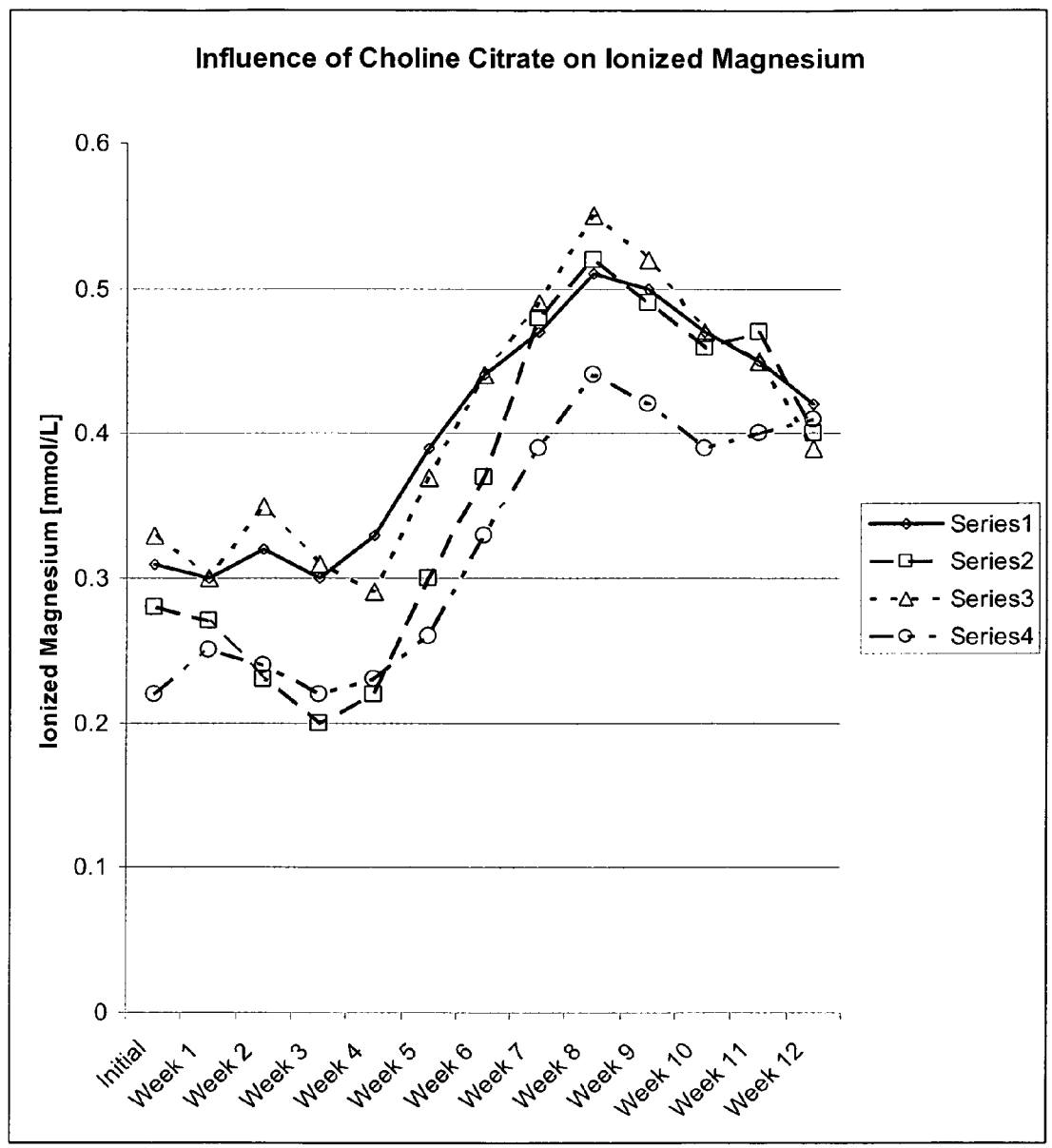
FIG. 1 is a graph showing the influence of choline citrate on ionized magnesium concentration in plasma.

This invention includes magnesium complexes and methods of administering magnesium to a mammal. It has been found that by administering to a mammal a magnesium salt, a quaternary amine or phosphatide and a di-carboxylic acid or tri-carboxylic acid, magnesium uptake in the subject could be improved.

The magnesium salt can be any known magnesium salts or a combination of several known magnesium salts. Preferred magnesium salts include, magnesium glycinate, magnesium ascorbate, magnesium chloride, magnesium sulfate, magnesium orotate, magnesium citrate, magnesium fumarate, magnesium malate, magnesium succinate, magnesium tartrate and magnesium carbonate.

The quaternary amine or phosphatide can include any quaternary amine, phosphatide or a combination of quaternary amines and phosphatides. A preferred quaternary amine is choline.

The di-carboxylic acid or tri-carboxylic acid can include any di-carboxylic acid, tri-carboxylic acid or combination of di-carboxylic acids and tri-carboxylic acids. A preferred tri-carboxylic acid is citrate.

Preferably the magnesium salt, the quaternary amine or phosphatide and the di-carboxylic acid or tri-carboxylic acid are administered concurrently. Concurrently, as used in herein, means administered within the same day. Preferably, they are administered together either as part of the same complex, which could include, for example a solution or a pill containing all of the components, or administered one after the other so that they can be metabolized together.

Preferably, the magnesium salt, the quaternary amine or phosphatide and the di-carboxylic acid or tri-carboxylic acid are administered as part of a complex in an aqueous glycerol or acqueous-glycerol solution. More preferably, the magnesium salt, the quaternary amine or phosphatide and the di-carboxylic acid or tri-carboxylic acid are administered as part of a complex in a solution containing both water and glycerol. Preferably, the solution contains approximately the same amount of water as glycerol.

The invention will be better understood with reference to the following examples in which subjects that had maladies associated with low magnesium levels were given a variety of combinations of compounds to determine there effectiveness.

The subjects in the examples were selected for signs of magnesium deficit including muscle irritability and fasciculation, benign cardiac irritability and/or moderate fibromyalgia pain that had previously been unresponsive to magnesium therapy.

Example 1

A 26 year old man suffering from supraventricular arrythmias was unresponsive to medication and, despite detailed medical workup, was determined to be 'idiopathic'.

Clinical assessments were done over periods of one month. Magnesium salts were administered to the subject for one month followed by one month of choline citrate alone followed by one month of magnesium salts along with concurrent administration of choline citrate.

During this time the patient was instructed to count the number of irregular heart beats (IHB) over a 2 minute period on rising and before bed. The average number of irregular heart beat counted over the three month time period can be found in table 1:

TABLE 1

|  | AM | PM | Total |
|---|---|---|---|
| Month 1 (ave) | 13 | 22 | 35 |
| Month 2 (ave) | 11 | 27 | 38 |
| Month 3 (ave) | 1 | 3 | 4 |

As shown in table 1, the average number of irregular heart beats decreased drastically when the magnesium salts were administered along with concurrent administration of choline citrate.

Example 2

A 72 year old woman suffering from ectopic heart beats which were unresponsive to medication and, despite detailed medical workup, was determined to be 'idiopathic'.

Clinical assessments were done over periods of one month. Magnesium salts were administered to the subject for one month followed by one month of choline citrate alone followed by one month of magnesium salts along with concurrent administration of choline citrate.

During this time the patient was instructed to count the number of irregular heart beats (IHB) over a 2 minute period on rising and before bed. The average number of irregular heart beat counted over the three month time period can be found in table 2:

TABLE 2

|  | AM | PM | Total |
|---|---|---|---|
| Month1 (ave) | 18 | 20 | 38 |
| Month2 (ave) | 22 | 19 | 41 |
| Month3 (ave) | 1 | 2 | 3 |

As shown in table 2, the average number of irregular heart beats decreased drastically when the magnesium salts were administered along with concurrent administration of choline citrate.

Example 3

A 59 year old man suffered from 'restless legs' and intermittent leg cramps during sleep. Clinical assessments were done with the subject taking magnesium salts for weeks 1 and 2, followed with the subject taking choline citrate alone for weeks 3 and 4, followed with the subject taking magnesium salts along with concurrent administration of choline citrate in weeks 5-9.

Each week the subject was asked to rate the intensity of the problem on a consistent rating scale with '0' indicating no problem and '100' indicating the most severe expression of the condition. The results can be found in table 3.

TABLE 3

| | Ave. intensity of leg cramp related difficulty |
|---|---|
| Week 1-2 | 88 |
| Week 3-4 | 83 |
| Week 5 | 63 |
| Week 6 | 44 |
| Week 7 | 29 |
| Week 8 | 12 |
| Week 9 | 7 |

As shown in table 3, the average intensity of the leg cramp related difficulty decreased drastically when the magnesium salts were administered along with concurrent administration of choline citrate.

The clinical assessments shown in Examples 1-3, are consistent with enhanced magnesium uptake when the correct magnesium salts are properly combined with high purity choline citrate.

Example 4

Subjects were selected for signs of magnesium deficit including muscle irritability and fasciculation, benign cardiac irritability and/or moderate fibromyalgia pain that had previously been unresponsive to magnesium therapy.

The subjects were put on a fixed dose of magnesium salts, 2 capsules with each meal (6 per day) for one month. For the second month, the same regimen was continued plus the addition of 1 teaspoon of choline citrate in juice or water taken at the same time as the magnesium supplement. For the third month, the subject continued the magnesium regimen but without the addition of choline citrate. Diet and fluid intake were kept consistent during the study interval.

The amount of magnesium in each subject was measured at the end of each week using an ion specific electrode. The reference range for ionized magnesium using this ion specific electrode (NOVA) is 0.43-0.59 mmol/L. The results can be found below in table 4.

TABLE 4

| | Subject: | | | |
| --- | --- | --- | --- | --- |
| | Series #1 Ionized Mg [plasma] | Series #2 Ionized Mg [plasma] | Series #3 Ionized Mg [plasma] Initial value | Series #4 Ionized Mg [plasma] |
| Results: | 0.31 mmol/L | 0.28 mmol/L | 0.33 mmol/L | 0.22 mmol/L |
| Week 1 | 0.30 | 0.27 | 0.30 | 0.25 |
| Week 2 | 0.32 | 0.23 | 0.35 | 0.24 |
| Week 3 | 0.30 | 0.20 | 0.31 | 0.22 |
| Week 4 | 0.33 | 0.22 | 0.29 | 0.23 |
| Week 5 | 0.39 | 0.30 | 0.37 | 0.26 |
| Week 6 | 0.44 | 0.37 | 0.44 | 0.33 |
| Week 7 | 0.47 | 0.48 | 0.49 | 0.39 |
| Week 8 | 0.51 | 0.52 | 0.55 | 0.44 |
| Week 9 | 0.50 | 0.49 | 0.52 | 0.42 |
| Week 10 | 0.47 | 0.45 | 0.47 | 0.39 |
| Week 11 | 0.45 | 0.47 | 0.45 | 0.40 |
| Week 12 | 0.42 | 0.40 | 0.39 | 0.41 |

FIG. 1, is a graphical representation of the data of table 4. As shown in FIG. 1 and table 4, the amount of magnesium in the subject's plasma increased to its higher values following weeks 5-8 when the subjects were taking choline citrate along with the magnesium salts.

In other studies, the role of choline citrate on magnesium levels in the absence of magnesium supplementation was evaluated. A modest but statistically insignificant increase in magnesium was noted over a 30 day period of evaluation.

The examples show that a previously unknown and unanticipated benefit is observed in the form of facilitated magnesium uptake when choline citrate is concurrently administered. Choline citrate alone does not substantially raise ionized magnesium levels. In some people with clinical magnesium need, even the most soluble and ionized forms of magnesium are less available, possibly because of inhibition of the Ca/Mg ATPase pump. A possible mechanism of action is the formation of micelles containing 2 molar equivalents of magnesium and choline along with 3 molar equivalents of citrate thus forming an electrically neutral complex.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

What is claimed is:

1. A magnesium complex consisting of:
   a magnesium salt;
   a phosphatide;
   a di-carboxylic acid or tri-carboxylic acid; and
   a water and glycerol solution.

2. The magnesium complex of claim 1, wherein the magnesium salt is selected from the group consisting of magnesium glycinate, magnesium ascorbate, magnesium chloride, magnesium sulfate, magnesium orotate, magnesium citrate, magnesium fumarate, magnesium malate, magnesium succinate, magnesium tartrate, and magnesium carbonate.

3. The magnesium complex of claim 1, wherein said complex consists of a magnesium salt, a phosphatide, a tri-carboxylic acid, and a water and glycerol solution.

4. The magnesium complex of claim 3, wherein the phosphatide is phosphatidyl choline.

\* \* \* \* \*